United States Patent [19]

James

[11] Patent Number: 4,814,868

[45] Date of Patent: Mar. 21, 1989

[54] APPARATUS AND METHOD FOR IMAGING AND COUNTING MOVING PARTICLES

[75] Inventor: Richard K. James, Redmond, Wash.

[73] Assignee: Quadtek, Inc., Redmond, Wash.

[21] Appl. No.: 104,764

[22] Filed: Oct. 2, 1987

[51] Int. Cl.$^4$ ............................................. H04N 7/18
[52] U.S. Cl. ................................... 358/100; 358/107
[58] Field of Search .............. 358/100, 107, 93, 113, 358/101, 105; 382/8, 23, 28; 364/557; 356/335, 372; 377/6, 10

[56] References Cited

U.S. PATENT DOCUMENTS

| | | | |
|---|---|---|---|
| 4,136,950 | 1/1979 | Labrum et al. | 358/105 X |
| 4,288,162 | 9/1981 | Sakamoto et al. | 356/335 |
| 4,319,270 | 3/1982 | Kimura et al. | 358/100 X |
| 4,320,915 | 3/1982 | Jones | 358/105 |
| 4,463,437 | 7/1984 | Schenck et al. | 358/107 X |
| 4,493,105 | 1/1985 | Beall et al. | 358/107 X |
| 4,539,588 | 9/1985 | Ariessohn et al. | 358/113 |
| 4,554,832 | 11/1985 | Hasegawa et al. | 358/107 X |
| 4,561,104 | 12/1985 | Martin | 358/100 X |
| 4,661,985 | 4/1987 | Akatsu | 358/107 X |
| 4,695,881 | 9/1987 | Kennedy et al. | 358/100 |
| 4,737,844 | 4/1988 | Kohola et al. | 358/100 |

OTHER PUBLICATIONS

R. E. Harrison et al., "Application of a Smelt Bed Imaging System", 1985 International Chemical Recovery/TAPPI Proceedings, pp. 153–158.

Primary Examiner—John W. Shepperd
Assistant Examiner—Victor R. Kostak
Attorney, Agent, or Firm—Christensen, O'Connor, Johnson & Kindness

[57] ABSTRACT

A video imaging and counting system for use in counting moving particles. A video camera (14) is used to monitor the interior of a boiler (12) for carryover particles (46) of burning fuel. A video signal produced by the camera is electronically filtered according to a software algorithm implemented by a microcomputer (116). The video signal is digitized and at least a portion of it is processed and filtered to eliminate the fixed background noise, and variations in illumination across each image. Hot particles appearing as streaks in the image are counted when adjacent time/spatially filtered data points exceeding a threshold level lie in a defined ranged of angular trajectories. The range conforms to the expected motion of a particle entrained in hot gas flow within the area of interest in the boiler. An enhanced image of the moving particles filtered by a similar algorithm and the particle count are displayed on a video monitor (22).

30 Claims, 6 Drawing Sheets

APPARATUS AND METHOD FOR IMAGING AND COUNTING MOVING PARTICLES

TECHNICAL FIELD

This invention generally pertains to an apparatus and method for counting objects, and more specifically, is directed to imaging and counting moving particulate matter using a video camera.

BACKGROUND OF THE INVENTION

The use of video imaging technology for monitoring conditions inside a furnace or boiler is well known in the prior art. In a typical application of such technology, a video camera is set up to monitor the condition of the boiler flame, so that adjustments to the fuel/air ratio and other operating parameters may be carried out. A display monitor provides an operator with a visual indication of the flame, as each parameter is adjusted.

In a related application of this technology, video imaging of the combustion area in a kraft pulp recovery boiler has proven useful in improving the boiler's operating efficiency. An example of such an imaging system is disclosed in U.S. Pat. No. 4,539,588 wherein a vidicon camera sensitive to light having a wavelength in excess of one micrometer is used for viewing the hot surface of a smelt bed in the bottom of a kraft recovery boiler. By monitoring the visual condition of the smelt bed, the operator can adjust the height of the bed and its configuration to achieve higher efficiency, faster turn-around following shutdowns, and greater boiler stability. The patent teaches that is is preferable to filter out visible light from the image, excluding all but a narrow band of wavelengths (70 nanometers wide) centered at 1,680 nanometers, to avoid interference from fumes and hot gases that overlie the smelt bed.

A problem in kraft recovery boilers not addressed by the above patent relates to the carryover of burning fuel particles into the upper portions of the boiler. Although this problem exists in other types of boilers to some extent, it is particularly troublesome in boilers used to recover pulping chemicals from the "black liquor" produced during the wood pulping process. Black liquor includes inorganic salts, e.g., sodium carbonate and sodium sulfate, mixed with wood pulp lignin and water, which are recovered by burning the black liquor (as a fuel) in a recovery boiler. Optimization of air distribution, fuel nozzle type, fuel distribution, percentage air/fuel and other parameters are important in the operation of such boilers to avoid an excessive quantity of the burning fuel particles from being carried into an upper portion of the boiler where they may plug passages in the boiler tubes, resulting in undesirable shutdowns and too frequent requirement for cleaning. In addition, the presence of excessive burning fuel particles in the upper portion of the boiler is an indication of incomplete fuel combustion, implying reduced operating efficiency. Often, the first sign of excessive burning particle carryover is an indication that the passages between the boiler tubes have become plugged, requiring shutdown of the boiler for cleaning.

The extent to which burning particles are being carried out of the combustion area of the boiler is difficult to monitor with prior art technology. Most conventional imaging systems such as that of the above-described patent are designed for monitoring conditions deep inside a boiler, and use a video camera with a respone time that is too slow to provide a clear image of the fast moving burning fuel particles. In addition, because of the greater depth of view and spectral sensitivity of such cameras, these particles are likely to be obscured by the background of the boiler interior.

The method most commonly used for checking the upper regions of the furnace for carryover particles is to conduct manual observations through an inspection port in the boiler wall. This procedure is hazardous to the operator due to the presence of noxious gases in the boiler, and because of the high temperatures to which the operator is exposed during the inspection. Consequently, such inspections are typically made on an infrequent basis, or not at all. Furthermore, such an inspection yields only a qualitative and very subjective evaluation of carryover conditions.

Clearly, an imaging system for monitoring the upper portions of a boiler for burning particles would avoid such hazards. However, even if such imaging systems were presently available, a video camera cannot directly quantitize the relative density of such particles, any more than a manual inspection. A quantitative assessment of the relative amount of burning particle carryover is required to properly evaluate the effect of adjustments made to the operating parameters of the boiler. Probes have been developed for monitoring carryover particles, but have not found widespread application, due to their requirements for maintenance, their cost, and the difficulty of interpreting the data they produce.

Accordingly, it is an object of this invention to provide an apparatus and method for imaging moving particles, minimizing the interference of noise, fixed background, obscuring fumes and hot gases, and varying illumination levels.

Another object is to quantitatively count the particles passing through a defined region of space.

A further object is to count fast moving particles using a video imaging device, the particles appearing in the image produced by the imaging device as streaks.

These and other objects of the invention will be apparent from the attached drawings and the disclosure of the preferred embodiment that follow hereinbelow.

SUMMARY OF THE INVENTION

The present invention is directed toward an apparatus and method for quantitatively monitoring moving particles within a region of interest. Imaging means are disposed, proximate the region that is to be monitored, and are operative to produce a video signal corresponding to an image of that region and of any moving particles present therein. Signal processing means are connected to the imaging means, in receipt of the video signal, which is processed thereby to eliminate noise and non-moving objects. The signal processing means produce a filtered signal including a plurality of data points corresponding to at least a portion of the image from which the effect of both gradual variations in intensity across the image and the background have been substantially reduced.

Counting means that are connected to the signal processing means count the occurrence of moving particles in the monitored region as a function of the relative magnitude of the data points in the filtered signal and a predetermined threshold level. The particle count is incremented by the counting means each time data points in the filtered signal representing a bright streak in the image caused by a moving particle exceeds the predetermined threshold level. Alternatively, if the particles are dark, the particle count is incremented each time the data point is less than the predetermined threshold level.

The imaging device produces a video signal that includes a plurality of scan lines. In the method for counting moving objects, each scan line is digitized producing a digitized signal including a plurality of pixels. A time averaged value for each a plurality of corresponding pixels in successive images is determined. The time averaged value for each such pixel of prior imges is then subtracted from corresponding pixels of a current digitized signal. This subtraction step filters out the fixed background, producing a time filtered signal.

Spatially adjacent pixels in the time filtered digitzed signal are arithmetically combined to discriminate between an abrupt change in the magnitude of adjacent pixels caused by a relatively narrow pulse in the video signal characteristic of a particle and a gradual change caused by a relatively wide pulse characteristic of variations in light intensity across the image, producing a time/spatially filtered digital signal. As a further step in discriminating between streaks due to moving particles and flashes of light or noise in the image, the particle count is incremented only when adjacent pixels in the time/filtered video signal all exceed a predetermined threshold, and when such pixels are aligned within a predefined angular range. Since the moving particles are entrained in a hot gas, it follows that their motion should generally conform to the expected movement of the gas, i.e., should move in a direction consistent with the direction of as flow. In addition, requiring a plurality of aligned pixels to exceed the threshold level discriminates between noise in the time/spatially filtered signal that might occur on one or two pixels, and the levels of adjacent pixels comprising the streak made by a moving particle.

In producing the video signal, a video camera particularly sensitive to light having a wavelength in the range between 700 and 1000 nanometers is preferably used. A substantial portion of the light radiating from hot particles lies within this range. Electronic filtering means are operative to produce a filtered analog video signal in which the moving hot particles are more clearly defined. Display means, connected to the electronic filtering means, are operative to display a visible image of light emitting hot particles, which appear as streaks in a single frame of the image due to the motion of the particles.

BRIEF DESCRIPTION OF THE DRAWINGS

FIG. 2 is a cutaway side view of an enclosure and a video camera contained therein, the video camera being used for imaging hot moving particles in the interior of a recovery boiler;

DESCRIPTION OF THE PREFERRED EMBODIMENT

Figure 1:
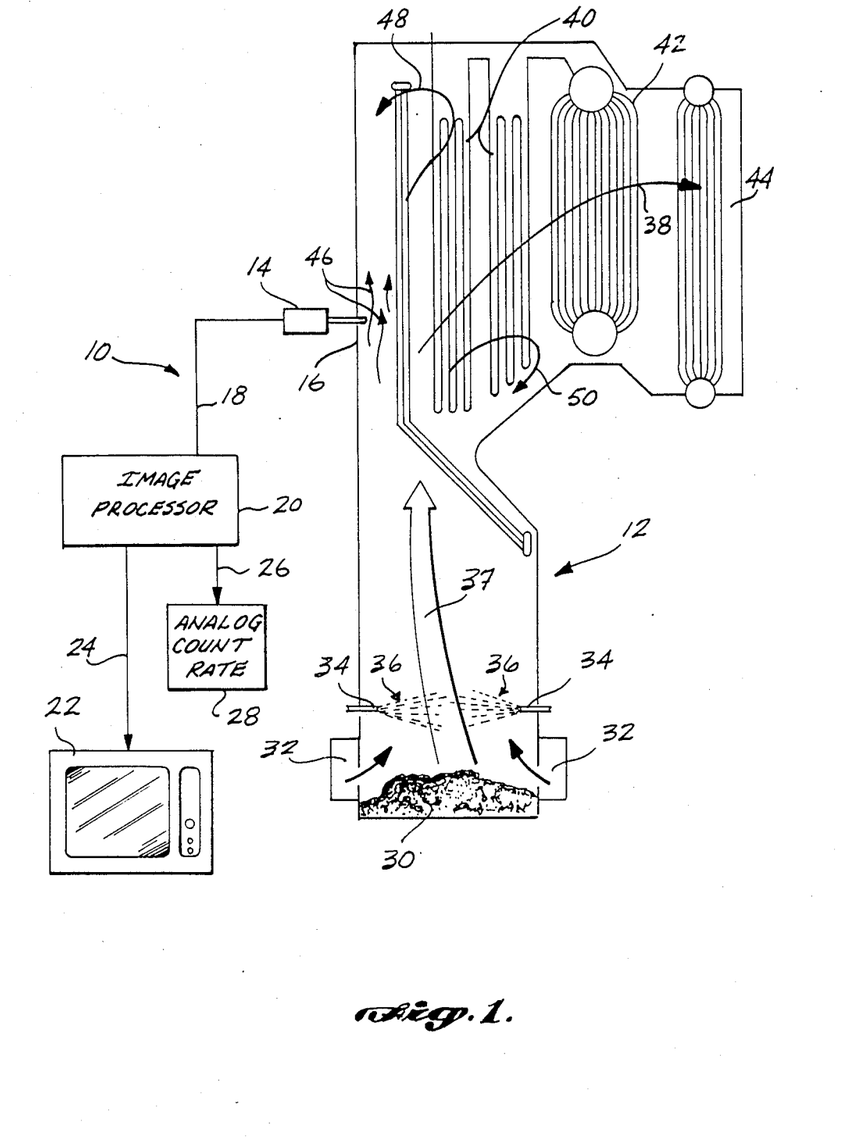
FIG. 1 illustrates schematically a recovery boiler, and application of an imaging device to monitor, display, and count carryover particles inside the upper portion of the boiler.

With reference to FIG. 1, a particle imaging and counting system generally denoted by reference numeral 10 is represented schematically in relationship to its use with a recovery boiler 12. The particle imaging and counting system 10 includes a video camera 14 disposed proximate the upper portion of recovery boiler 12, so as to view the interior of the boiler through an opening in a boiler wall 16. Video camera 14 produces an analog video signal corresponding to the image of the interior of boiler 12 within view of the camera, which is conveyed via conductor 18 to an image processor 20. Image processor 20 digitizes the analog video signal, producing a digital signal corresponding to a region of interest viewed within boiler 12, and processes the digital signal to minimize the effects of noise, fixed background, changes in illumination, and other aspects of the signal that tend to obscure and inhibit detection of moving particles of burning fuel in the boiler. An analog video signal representing a digitally enhanced and filtered version of the signal from video camera 14 is output by image processor 20 via conductor 24 to drive a video display (or monitor) 22. An image of carryover particles within the field of view of video camera 14 is thus constantly displayed to a boiler operator. In addition, image processor 20 produces an output signal on conductor 26 for driving an analog count rate meter 28 and/or providing a count rate signal for input to a data logging system (not shown) associated with the boiler.

Although particle imaging and counting system 10 may be used in a variety of applications, it is particularly well suited for monitoring the occurrence of carryover particles of hot burning fuel in a kraft recovery boiler in which black liquor is burned. As explained above, such boilers are particularly susceptible to problems associated with excessive carryover particles plugging the passages between the boiler tubes, necessitating shutdown of the boiler for cleaning. If operation of the kraft recovery boiler is properly monitored and controlled to avoid excessive burning particle carryover in the upper portion of the boiler, the time intervals between shutdowns for cleaning and maintenance may be greatly extended and, in addition, the efficiency of the boiler system substantially improved.

In the schematic representation of boiler 12 shown in FIG. 1, black liquor fuel enters the boiler through fuel nozzles 34 as a coarse spray 36. Combustible organic constituents in the black liquor burn as the fuel droplets mix with air. Sodium sulfate in the fuel is chemically converted to sodium sulfide in the reducing zone of the bed. The inorganic salts drop to the floor of the boiler forming a smelt bed 30, from which liquid is drained. Combustion air enters the combustion zone (immediately above smelt bed 30) through ports 32 on four sides of boiler 12. Ideally, combustion of substantially all of the black liquor fuel should be carried out in the lower portion of boiler 12, well below the boiler tubes that are disposed in its upper portion. However, depending on adjustment of various operating parameters, hot gases from the combustion process may entrain burning fuel particles, carrying them upward into the boiler tube passages, as shown by arrow 37.

Video camera 14 is disposed outside the upper portion of the boiler, adjacent an interior section in which the direction of flow of the hot gases is well defined. As shown in FIG. 1, hot burning fuel particles 46 entrained within the moving gases tend to follow a generally vertical flow pattern in the portion of the boiler 12 viewed by video camera 14. In other boiler designs in which the hot gases may be flowing in a different direction, the video camera may be mounted in a different location, as appropriate to view carryover particles. However, it is important to avoid mounting video camera 14 in areas where the hot gases tend to eddy, such as the areas of boiler 12 where gas flow is indicated by curved arrows 48 and 50, since the direction in which the burning fuel particles would be moving in these locations is somewhat unpredictable. Hot air from the combustion process in the lower portion of the boiler flows first through the superheater tubes 40 and then through the steam generator tubes 42, exiting through an economizer port 44. Water passing through superheater tubes 40 and steam generator tubes 42 is converted into superheated steam, and may be used for producing electrical power in a turbine generator, or as a source of heat in other processes. Excessive amounts of carryover of burning particles impacting upon superheater tubes 40 and/or steam generator tubes 42 tend to form deposits which plug the passages between the tubes, reducing boiler efficiency and eventually causing shutdown of the boiler.

As shown in greater detail in FIG. 2, video camera 14 is disposed to monitor the interior of boiler 12 through a window or porthole 64 formed in boiler wall 16. A lens 60 of camera 14 extends through porthole 64, and includes a plurality of lens elements (not shown) cooled by an airflow. The lens cooling airflow enters via line 62, passes around the lens elements along the length of lens 60, and exits through a port 63 that is disposed on an end of the lens extending into the boiler.

Video camera 14 is mounted on a support plate 70 within a thermally insulating environmental enclosure 72. An autoiris attachment 68 is disposed between lens 60 and a video detector (not shown) within camera 14, to control the amount of light reaching the detector in response to a control signal input over conductor 74. An optional optical filter 66 is disposed within the light transmission path of lens 60 to filter out light having a wavelength outside the range of interest described below. The analog video signal produced by camera 14 is conveyed by conductor 76 to a connector 78 disposed on the rear of environmental enclosure 72. Conductor 18 (FIG. 1) is normally attached to connector 78.

Video camera 14 is chosen to be sensitive to light in the near infrared portion of the spectrum in the range from 700–1000 nanometers, since the radiation emitted from the hot burning fuel particles is particularly strong in this range of wavelengths. The fumes in a recovery boiler tend to scatter light having a wavelength in the range of 700–1000 nanometers, which obscure the background beyond the near field of view, providing a high contrast for the particles relative to the boiler interior. Optical filter 66 is optional, but if specified to pass wavelengths in excess of 650 nanometers, helps to reduce intererence from fumes and sodium yellow light by excluding visible light wavelengths below this limit. A typical optical filter 66 would transmit fifty percent of incident light at the 650 nanometer wavelength.

Video camera 14 may be either a solid-state or tube-type camera, having a spectral sensitivity covering the above-defined 700–1000 nanometer range of wavelengths. An RCA series 2000 ULTRACON TM camera is used in the preferred embodiment for this purpose. It is anticipated that a camera using a charged coupled device (CCD) detector would also perform well in this application. A line scan device that is designed to scan a single line at one time is encompassed by the term video camera. Likewise, the term video signal is intended to encompass a plurality of temporally sequential lines produced by a line scan device.

Figure 5:
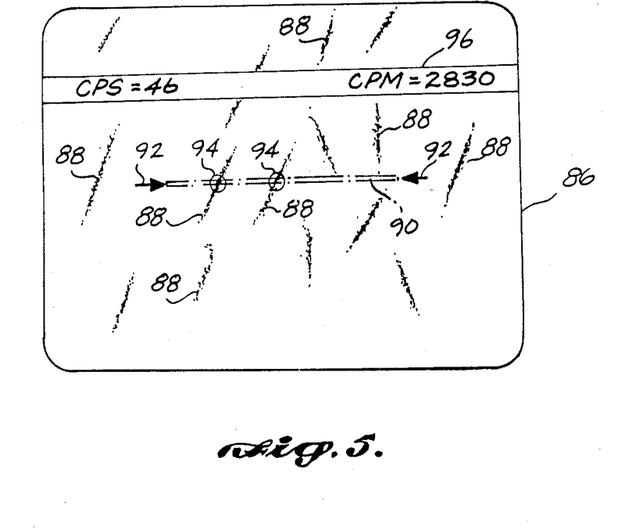
FIG. 5 illustrates an image produced on a video display comprising the present invention.

Turning now to FIG. 5, an image 86 is shown representing a single video frame as it would appear on video display 22, following filtering and enhancement by image processor 20. The hot burning fuel particles 46 (FIG. 1) are moving with such speed, that they appear as streaks 88 in the single frame of image 86, rather than as individual points. In addition to the streaks representing burning fuel particles, image 86 includes a text bar 96 that shows the number of burning particles counted during the previous second and a running average of the number of particles counted per minute. Rather than counting particles across the entire displayed image, image processor 20 counts particles passing through a relatively small zone 90 disposed approximately in the vertical center of image 86, between arrows 92. The ends of zone 90 are purposely inset from each side of the image to avoid edge anomalies in the video signal. Image processor 20 produces a circle 94 around each of the moving particles (streaks 88) passing through zone 90 in the image 86 to indicate that the particle has been counted. Only those particles passing through zone 90 ae counted, the count serving as a relative indication of carryover particle density in the field of view of camera 14. Text bar 96 is generated on video display 22 by image processor 20 to facilitate a quantitative digital evaluation of particle density in the upper portion of boiler 12, relative to the qualitative visual display of the particles. By placing a circle 94 on each streak 88 that has been counted as a particle, image processor 20 provides positive assurance that all particles passing through zone 90 have been counted, and that flashes of light in the background have not been counted.

Figure 6:
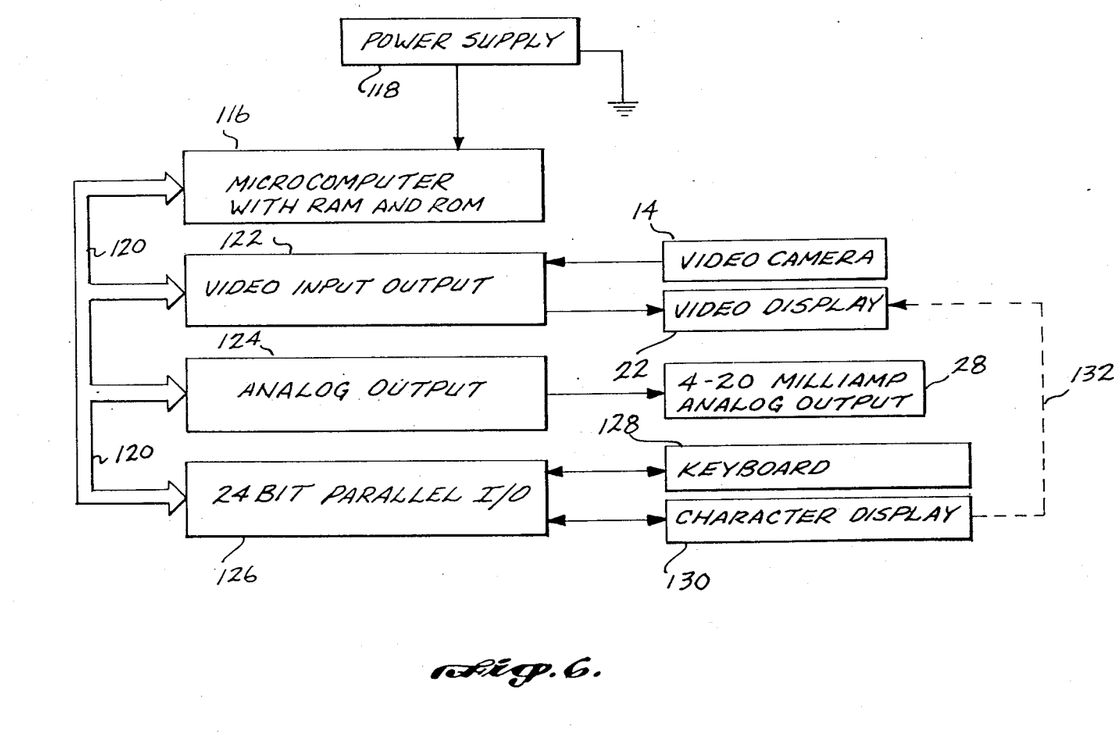
FIG. 6 is a block diagram of an image processing system comprising the present invention.

Referring to FIG. 6, a block diagram of image processor 20 is shown. The image processor includes a microcomputer 116 having onboard random access memory (RAM) and read-only memory (ROM). In the preferred embodiment, microcomputer 116 is compatible with the IBM AT-BUS computer system and includes an INTEL 80286 microprocessor. It is contemplated that other types of digital processors could be used for this purpose, including a dedicated video signal processor, perhaps encompassing the functions of other elements of the image processor. A data bus 120 is connected to microcomputer 116, providing a passive backplane for connection to video input/output board 122, analog output board 124, and 24-bit parallel I/O board 126. Video input/output board 122 digitizes the video analog signal produced by video camera 14 into an 8-bit digital value for each of 480 lines by 512 pixels of a given video frame. The digitized video signal is modified under control of microcomputer 116 and output as an analog video signal to video display 22. As described in greater detail below, microcomputer 116 uses the digitized video signal to detect and count hot particles crossing zone 90. The particle count rate determined by microcomputer 116 is converted into an analog value by the analog output board 124 and is output as an analog count rate to a 4-20 milliamp panel meter (not shown) or alternatively, to the data logging system for the boiler mentioned above.

In the preferred embodiment, a hex keyboard 128 is used to provide control input to microcomputer 116 through 24-bit parallel I/O board 126. I/O board 126 is also used to provide a drive signal for a 20 character liquid crystal display (LCD) 130, used to display information input by keyboard 128 and output by microcomputer 116. A power supply 118 is provided for microcomputer 116, and the other power consuming elements of image processor 20 connected to bus 120.

Figure 3:
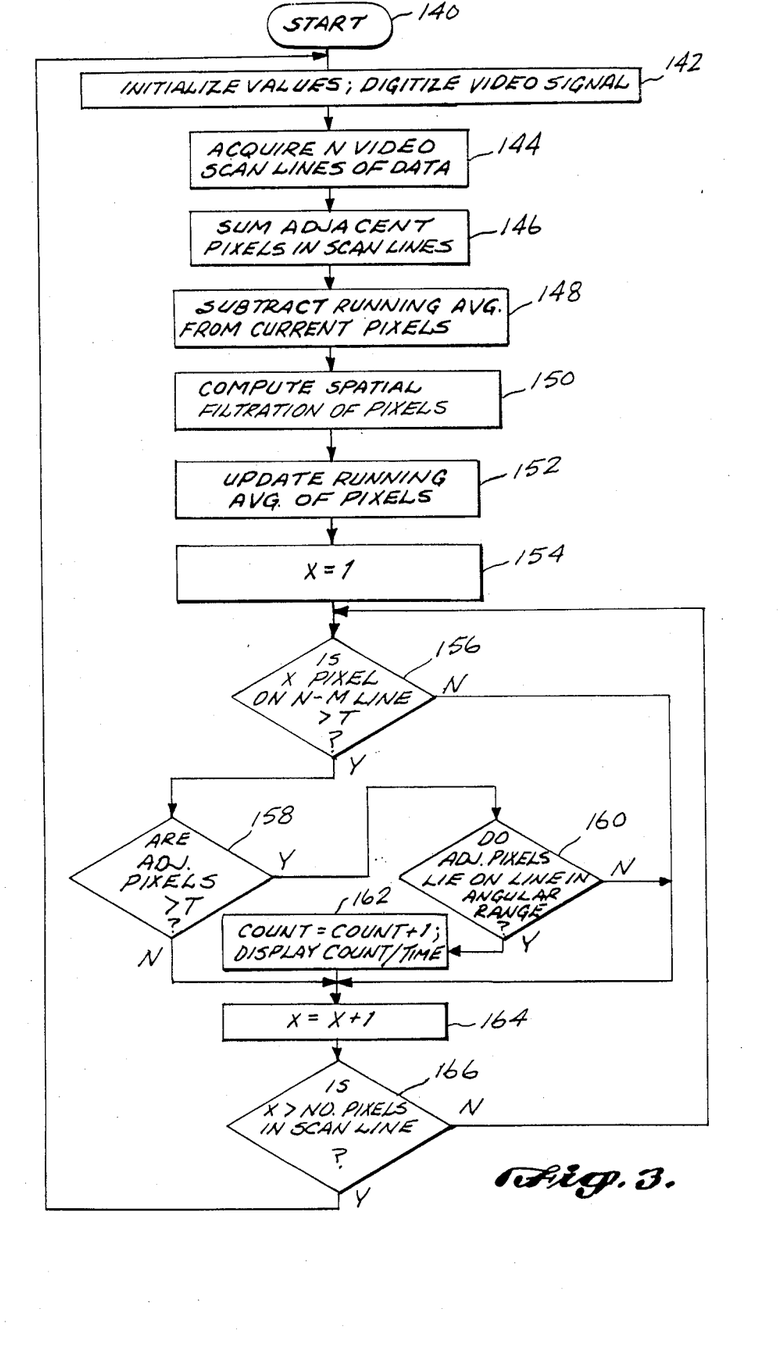
FIG. 3 is a flowchart showing the steps implemented by a microprocessor in processing a video signal for imaging and counting hot moving particles in a boiler.

A simplified flowchart showing the steps taken by microcomputer 116 to process the digitized video signal produced by video input/output board 122 is shown in FIG. 3. These program steps are stored as a machine language program in binary code within ROM on microcomputer 116.

The control algorithm flowchart begins with start block 140 and proceeds to block 142 wherein various variables in the program are initialized as required for processing successive video images produced by video camera 14. In addition, a complete frame of video information containing 480 horizontal lines with 512 8-bit data points on pixels per line is digitized into video memory (RAM) on microcomputer 116. (The terms "data point" and "pixel" and their plural forms are used interchangeably in the following description.) In block 144, a small number of those lines N represented as data points is copied into another portion of computer memory for analysis. N can vary from as few as one to as many as five lines, depending upon the degree of noise rejection desired, with more lines providing better noise rejection. In the preferred embodiment, N=3. When more than one line is copied into memory, it is important that the copied lines be scanned sequentially in time. Normally, an image comprising one frame of video signal is scanned in 1/30 second. For a typical interlaced video camera in which even and odd lines are scanned in successive groups, every other line should be copied for analysis, i.e., either even numbered lines or odd numbered lines may be copied, but not both. The lines copied into memory for analysis must be sequential in time because a particle streak will often appear only during the first 1/60 second that the even lines ae scanned, or during the next 1/60 second that the odd lines are scanned. The video data processing algorithm, as discussed further hereinbelow, relies on detecting the presence of a particle on adjacent lines, for noise rejection purposes.

In block 146, the video data from a number of adjacent pixels are summed together to reduce the data points per line to a fraction of the original 512; preferably every other point is summed, producing 256 points of video data. This reduces noise and the quantity of data to be processed in subsequent steps and improves the signal-to-noise ratio. Alternatively, each pixel in a scan line may be processed, or as many as five pixels may be summed together to reduce the number of data points per scan line to 102.

Data points resulting from summing adjacent pixels in each scan line as performed in block 146 will be referred to as the "summed video data." In block 148, corresponding points of the summed video data are subtracted from a running average for those points derived from preceding images produced by video camera 14. Implementing block 148 produces "time filted video data," and serves to eliminate or substantially reduce the effect of the background of the interior of boiler 12 viewed by video camera 14. Since the background portion of the imge viewed by video camera 14 is substantially the same in successive images, subtracting the time averaged value for corresponding data points from the present summed video data has the effect of filtering out the background in the time filtered video data. Only portions of the image that have changed over time are not filtered out by the subtraction process carried out in block 148. Thus, the effects of a fast moving particle appearing as a streak in the current video image will remain in the time filtered video data, whereas the effects of non-moving or static portions of the image are eliminaed or substantially reduced.

Continuing on to block 150, the time filered video data is spatially filtered according to the following mathematical algorithm:

$$F_i = (G + 1) V_i - \sum_{j=0}^{G} V_{i+j-G/2} \quad (1)$$

In Equation (1) shown above, $F_i$ is a value at a point i in the time/spatially filtered video data, $V_i$ is the time filtered video data for the ith point, and G is a filtering constant. Preferably, G is selected to equal a power of two to permit easy multiplication by microcomputer 116, and typically has a value of eight. Spatially filtering the time filtered data by application of Equation (1) has the effect of filtering out relatively gradual variations in light intensity across the image by computing the weighted difference between each data point $V_i$ in the time filtered data and the G/2 adjacent data points on each side of the point $V_i$. Clearly, many other algorithms might be used for filtering out gradual spatial changes in light intensity in the image. Equation (1) merely represents one approach for carrying out this function that is easily implemented by microcomputer 116.

Figure 7:
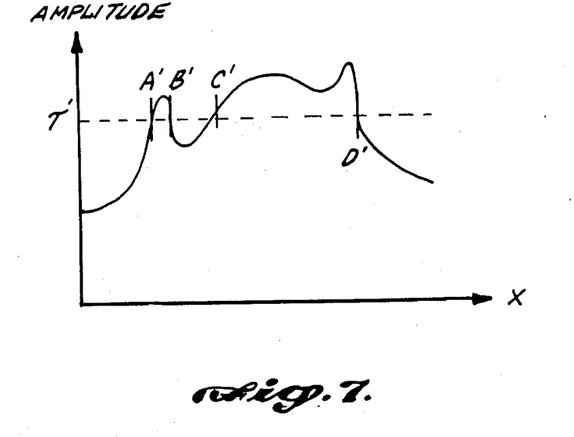
FIG. 7 is a graph illustrating the amplitude of a single scan line of the video signal, prior to spatial filtration; and, FIG. 8 is a graph similar to FIG. 7, showing the amplitude of the same scan line following spatial filtration.
Figure 8:
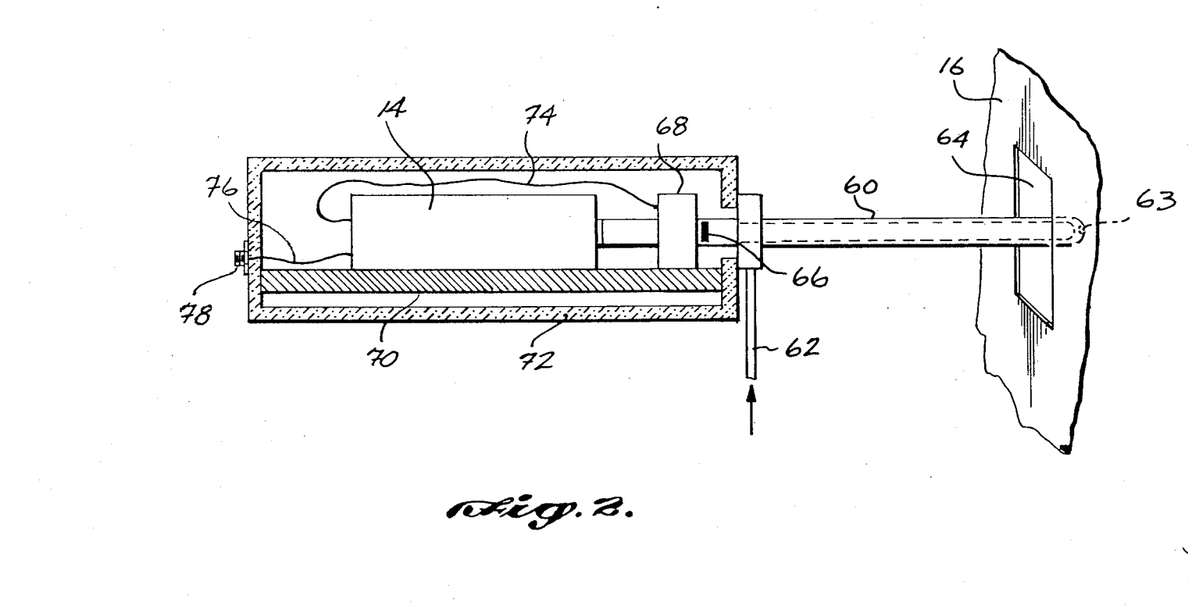

FIG. 7 illustrates the relative amplitude of a single exemplary scan line in the time filtered video data. The amplitude of the signal passes through a predefined threshold level T' in a narrow pulse, between A' and B', and also in a relative wide portion of the scan line length, between C' and D'. The narrow pule A'B' is likely due to a moving particle, but it is not apparent whether the wide portion C'D' is caused by a particle or by a flash of light appearing spatially in the central portion of the image. FIG. 8 illustrates the same scan line after the time filtered data is spatially filtered. By subtracting the values of adjacent data points from each pixel on the scan line, the gradual changes in intensity or amplitude are substantially reduced, defining two sharply defined narrow width pulses AB and CD, characteristic of particles. Comparison of FIGS. 7 and 8 should clarify the benefits provided by spatially filtering the time filtered data in block 150 of FIG. 3.

Continuing in FIG. 3, in block 152, the "running average" data used in block 148 is updated with the summed video data of the current image computed in block 146 by recomputing the running averaging with current summed video data added in. The updated running average determined in block 152 will be used for processing the next image provided by video camera 14. In block 154, a counter X is set equal to one. Counter X is used in block 156 to determine if the Xth data point on the N-M scan line exceeds a predetermined threshold value, T, where N equals the number of scan lines within zone 90 shown in FIG. 5 and M is a predefined integer less than N. In the preferred embodiment, N equals 3, and M equals 1. Thus, block 156 is preferably directed to determining whether the value of the Xth point on the middle scan line of the three scan lines in zone 90 is greater than the predetermined threshold value. This step is illustrated graphically in FIG. 8 where several data points at AB and at CD exceed the threshold level T. Assuming that the check of block 156 is answered affirmatively, in block 158, a check is made to determine if adjacent data points also have a value in excess of the threshold, i.e., in the time/spatially filtered data, to determine whether the X−1, X or X+1 data points in the first and third scan lines also exceed the threshold. If they do, in block 160, a determination is made whether the adjacent pixels exceeding the threshold lie on a line within a predetermined angular range. In the preferred embodiment, the predetermined angular range is plus or minus 45° relative to the vertical direction in the image 86 shown on video display 22. This direction corresponds to the direction of flow of the hot gases (represented by arrow 37) carrying particles 46 past video camera 14 in FIG. 1.

Figure 4:
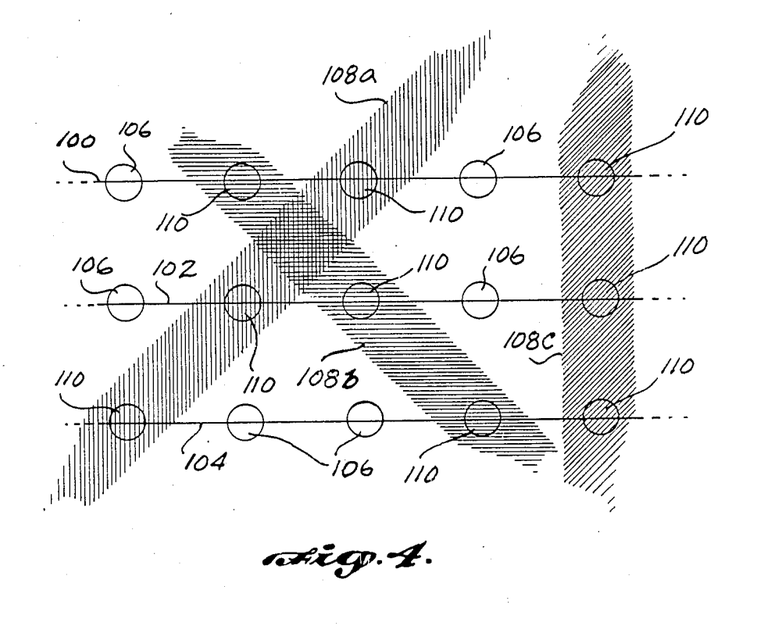
FIG. 4 is an enlarged schematic representation of a portion of a filtered signal, showing the possible combinations of adjacent pixels (data points) corresponding to a streak caused by a moving particle.

At this point, it is helpful to refer to FIG. 4, wherein a portion of three scan lines 100, 102, and 104 is shown, with pixels (data points) being represented by circles 106. Three sets of dash lines 108a, 108b and 108c are each intended to represent a portion of streaks 88 corresponding to moving particles as they may appear in three different orientations in video image 86 (FIG. 5). In FIG. 4, each set of dash lines 108 connects three pixels 110 all having an intensity or value that exceeds the predetermined threshold, T, checked in block 158 of FIG. 3. (Normally, three such particles would not be found so close together.) Moreover, each set of dash lines 108 lies on a line that a moving particle 46 entrained within the hot gases would follow through the zone of interest. The accepted angular range is ±45° relative to the direction of gas flow, i.e., ±45° about vertical in image 86. However, a streak represented by pixels 110 having an intensity in excess of the threshold, T, that extends horizontally along the same scan line, e.g., 100, would not satisfy the requirement checked in block 160 and would not be counted as a moving particle. More importantly, the step performed in blocks 156, 158 and 160 prevents one or two pixels that may exceed the threshold T due to noise from being counted as moving particles.

If three adjacent pixels 110 exceeding T are found in the proper angular range, microcomputer 116 increments COUNT by one, as shown in block 162 of FIG. 3. Thereafter, in block 164, the Xth data point on the N-M scan line is incremented by one, and in block 166, a check is made to determine if the value of X exceeds the total number of pixels in a scan line. If not, the algorithm repeats the procedure in block 156. Otherwise, microcomputer 116 proceeds to reinitialize values and digitizes another frame of the analog video signal at block 142. The value of COUNT achieved in block 162 for a given time period (determined by reference to an internal time base of microcomputer 116) is displayed either on the video display 22, or on a separate display such as character display 130. Optionally, a running average of the counts/minutes may also be computed and displayed. A dashed line connects character display 130 to video display 22 in FIG. 6 to indicate that information shown on character display 130 may alternatively be shown on video display 22.

In an alternative application, relatively dark particles imaged against a brighter background may be counted by applying the same algorithm, except that in blocks 156 and 158, microcomputer 116 would check to determine if the Xth pixel and its adjacent pixels may have an intensity less than a predetermined threshold T. A nonradiant particle would thus produce a dark streak against a brighter background.

Although not shown in a separate flow chart, microcomputer 116 can implement a similar filtering algorithm to enhance and filter the image of the fast moving hot particles 46 of burning fuel shown on video display 22, by carrying out the steps in program blocks 140, 142, 148 and 152 of FIG. 3. Following start of the algorithm in block 140, in block 142, the microcomputer causes variables to be initialized and an entire frame of 512 pixels by 480 scan lines to be digitized. In block 148, a running average of all corresponding pixels in prior frames is subtracted from the corresponding pixels of the current frame, producing a "time filtered image." In block 150, each of the pixels of the time filtered image are spatially filtered by subtracting the sum of the values for G surrounding pixels (on all sides of the current pixel, i.e., in both the x and y dimensions) from the product of G and the current pixel, successively for each pixel in the frame. In block 152, the running average of pixels in prior frames is updated by adding in the pixels in the current image and recomputing the running average. Finally, the time/spatially filtered image is converted to an analog video signal and output by video input/output board 122 to drive video display 22. The background of the boiler is filtered out by the step in block 148, and gradual variations in brightness across the image are reduced by the spatial filtration step in block 150. As a result, the moving particles are more clearly visible on video display 22.

Although the particle imaging and counting system is particularly well suited for monitoring carryover particles in a kraft recovery boiler, it is contemplated that it may be used for other applications in which it is desirable to image and/or count objects or particulate matter in motion, whether radiant, dark, or illuminated. Thus, it is not limited for use in boilers or furnaces, but has utility in many other processes and systems.

While the present invention has been disclosed with respect to a preferred embodiment, those skilled in the art will understand that modifications thereto may be made within the scope of the claims that follow hereinbelow. Accordingly, the scope of the invention is to be determined entirely by reference to those claims and should not directly or by implication be limited by what has been disclosed as the preferred embodiment.

The embodiments of the invention in which an exclusive property or privilege is claimed are defined as follows:

1. Apparatus for quantitatively monitoring moving particles, comprising:
 (a) imaging means, disposed proximate a region to be monitored, for producing a video signal corresponding to an image of said region and of any moving particles that may be present therein;

(b) signal processing means, connected to the imaging means, for processing the video signal to eliminate noise in the video signal and non-moving objects comprising the image, said signal processing means being operative to produce a filtered signal including a plurality of data points corresponding to at least a portion of the image from which the effect of both gradual variations in intensity across the image and a fixed background have been substantially reduced; and (c) counting means, connected to the signal processing means, for counting moving particles in the monitored region as a function of the relative magnitude of the data points in the filtered signal and a predetermined threshold level.

2. The apparatus of claim 1, wherein an additional count is registered by the counting means each time data points in the filtered signal representing a bright streak in the image caused by a moving particle exceed the predetermined threshold level.

3. The apparatus of claim 1, wherein an additional count is registered by the counting means each time data points in the filtered signal representing a dark streak in the image caused by a moving particle are less than the predetermined threshold.

4. The apparatus of claim 1, wherein the imaging means comprise an optical lens, and a detector sensitive to light having a wavelength in the range between 700 and 1000 nanometers.

5. The apparatus of claim 1, wherein the signal processing means are operative to digitize the video signal.

6. The apparatus of claim 5, wherein the signal processing means comprise a digital processor having an electronic memory in which is stored a program for processing the digitized video signal and filtering the digitized video signal to produce the filtered signal.

7. The apparatus of claim 6, further comprising means for producing a filtered analog video signal corresponding to the filtered signal and means for displaying an image of the moving particles in response to the filtered analog video signal.

8. In a combustion device, apparatus for counting and monitoring the relative density of hot particles, said apparatus comprising:

(a) a video camera disposed outside the combustion device, and positioned to view a region of interest in its interior through a port formed in a side of the combustion device, producing a video signal corresponding to an image of the interior of the combustion device and of hot particles that may be present in said region of interest, said hot particles appearing as streaks in the image;

(b) an image digitizer, connected to the video camera and operative to produce a digital signal corresponding to the video signal;

(c) digital processor means, connected to the image digitizer in receipt of said digital signal, for processing said digital signal to:

(i) digitally filter a portion of the combustion device interior appearing as a fixed background in the image from the digital signal;

(ii) discriminate between noise in the digital signal and streaks corresponding to the moving hot particles; and (iii) produce a hot particle count signal for each streak detected; and (d) counting means, connected to the digital processor means, for accumulating the total number of hot particles detected by the digital processor means during a predefined period of time in response to the hot particle count signal.

9. The apparatus of claim 8, wherein the digital processor means comprise a microprocessor.

10. The apparatus of claim 8, wherein the digital processor means are operative to subtract an average of the digital signals corresponding to prior images from a digital signal corresponding to a current image to filter out the fixed background in the image.

11. The apparatus of claim 8, wherein the digital signal comprises a plurality of data points and wherein the digital processor means are operative to spatially filter elements of the digital signal by arithmetically combining data points corresponding to spatially proximate elements of the image, to discriminate between an abrupt change in the magnitude of said data points caused by a relatively narrow pulse in the video signal characteristic of a particle, and a gradual change caused by a relatively wide pulse characteristic of variations in background light intensity across the image.

12. The apparatus of claim 8, wherein the video signal produced by the video camera corresponds to an image in the near infra-red light spectrum.

13. A method for counting moving radiant objects having a defined range of angular trajectories, comprising the steps of:

(a) scanning a region of interest through which the radiant objects might pass, using an imaging device;

(b) producing a video signal with said imaging device, said video signal including a plurality of scan lines;

(c) digitizing each scan line, to produce a digitized signal including a plurality of pixels, said digitized signal corresponding to an image of said region and of any radiant objects moving therethrough;

(d) determining a time averaged value for each of a plurality of corresponding pixels in the digitized signals of successive images;

(e) subtracting the time averaged value of the pixels of prior images from corresponding pixels of a current image digitized signal to eliminate fixed aspects of the image, producing a time filtered digitized signal;

(f) spatially filtering the time filtered digitized signal, by arithmetically combining spatially proximate pixels to discriminte between an abrupt change in the magnitude of proximate pixels caused by a relatively narrow pulse in the video signal characteristic of a particle, and a gradual change caused by a relatively wide pulse characteristic of variations in background light intensity across the image, producing a time/spatially filtered digitized signal;

(g) detecting a moving radiant object when adjacent pixels in the time/spatially filtered digitized signal exceeding a predetermined threshold are aligned within the defined range of angular trajectories; and (h) incrementing by one, a count of the moving radiant objects as each additional moving radiant object is detected.

14. The method of claim 13, wherein the defined range of angular trajectories correspond to the expected motion of a particle entrained in a fluid moving in a defined direction.

15. The method of claim 13, wherein the fixed aspects of the image comprise a background of the region of interest.

16. The method of claim 13, wherein the defined range of angular trajectoreei lies in the range ±45° relative to a defined direction within the region of interest.

17. A method for detecting and counting moving objects passing through a region of interest against a background of variable intensity illumination and visual noise, comprising the steps of:
  (a) scanning the region of interest with a video camera, producing a video signal corresponding to an image of said region and of any moving objects in said region, said image including a plurality of scan lines;
  (b) for a plurality of scan lines in each of a plurality of successive images in time, digitizing the video signal, producing a corresponding digital signal comprising a plurality of pixels in which the pixels are represented by digital numbers;
  (c) computing a running average over time of the digital numbers of corresponding pixels in successive images;
  (d) subtracting the running average digital numbers for the pixels of preceding images from the corresponding digital numbers of a current image to produce a time filtered digitized signal, in which the effect of non-moving objects in the image is substantially reduced;
  (e) spatially filtering the time filtered digitized signal, by arithmetically combining the digital numbers of spatially proximate pixels to discriminate between an abrupt change in the magnitude of the digital numbers of proximate pixels caused by relatively narrow pulse in the video signal characteristic of a particle, and a gradual change caused by a relatively wide pulse characteristic of variations in background light intensity across the image, producing a time spatially filtered digitized signal;
  (f) counting moving objects as a function of the relative magnitude of the digital numbers representing pixels in the time/spatially filtered signal and a predetermined intensity level.

18. The method of claim 17, wherein the moving objects are substantially brigher than the rest of the image, further comprising the step of incrementing the count if:
  (a) a digital number representing a pixel in the time/spatially filtered digital signal exceeds the predetermined intensity level; and
  (b) the digital numbers of a plurality of adjacent pixels exceed the predetermined intensity level; and
  (c) the adjacent pixels represented by the digital numbers exceeding said predetermined intensity level are aligned along a line.

19. The method of claim 17, wherein the moving objects are substantially darker than the rest of the image, further comprising the step of incrementing the count if:
  (a) a digital number representing a pixel in the time/spatially filtered digital signal is less than the predetermined intensity level; and
  (b) the digital numbers of a plurality of adjacent pixels are less than the predetermined intensity level; and
  (c) the adjacent pixels represented by digital numbers less than said predetermined intensity level are aligned along a line.

20. The method of claim 17, wherein said image is defined by light having a wavelength between 700 and 1000 nanometers.

21. The method of claim 17, wherein the moving objects are entrained in a fluid flowing in a generally prescribed direction, further comprising the step of incrementing the count if the relative magnitude of the digital numbers representing a plurality of adjacent pixels lying in a line within a defined angular range of the direction of fluid flow all exceed the predetermined intensity level.

22. The method of claim 21, wherein the defined angular range is centered about the prescribed direction of fluid flow, said range extending in an angle of up to ±45° relative to said direction.

23. The method of claim 17, wherein the moving objects radiate light in the near infrared spectrum.

24. Apparatus for displaying light emitting hot particles in a region of a combustion device remote from where fuel is injected, comprising
  (a) imaging means disposed adjacent the region of the combustion device through which the hot particles may pass and particularly sensitive to light having a wavelength in the range from 700 to 1000 nanometers, for producing a video signal corresponding to an image of said light emitting hot particles;
  (b) electronic filtering means, connected to the imaging means, for producing a filtered signal from which noise and any non-moving background elements in the image produced by the imaging means are substantially excluded; and
  (c) display means, connected to the electronic filtering means, for producing a visible image of the hot particles from the filtered signal.

25. The apparatus of claim 24, wherein the imaging means comprise a video camera.

26. The apparatus of claim 24, wherein the light emitting hot particles comprise carryover particles in a black liquor recovery boiler.

27. The apparatus of claim 24, wherein the display means comprise a video monitor on which the hot particles visually appear in each image as streaks.

28. The apparatus of claim 27, further comprising means for counting the hot particles passing through at least a portion of said region.

29. The apparatus of claim 28, wherein the display means are further operative to indicate an area of the image wherein the occurrence of visual streaks are counted and to display a digital count of the particles passing through said area during a predefined period of time.

30. The apparatus of claim 28, further comprising means for generating a visible marker on the visible image for each streak that has been counted.

* * * * *